(12) United States Patent
Furner (10) Patent No.: US 9,591,842 B2
(45) Date of Patent: Mar. 14, 2017

(54) PASSIVE VOLATILE DISPENSING DEVICE

(71) Applicant: S.C. Johnson & Son, Inc., Racine, WI (US)

(72) Inventor: Paul E. Furner, Racine, WI (US)

(73) Assignee: S. C. Johnson & Son, Inc., Racine, WI (US)

( * ) Notice: Subject to any disclaimer, the term of this patent is extended or adjusted under 35 U.S.C. 154(b) by 176 days.

(21) Appl. No.: 14/015,026

(22) Filed: Aug. 30, 2013

(65) Prior Publication Data

US 2015/0060565 A1 Mar. 5, 2015

(51) Int. Cl.
*A01M 1/02* (2006.01)
*A61L 9/12* (2006.01)
*A61L 9/04* (2006.01)
*B65D 83/00* (2006.01)
*A01M 1/20* (2006.01)

(52) U.S. Cl.
CPC ............ *A01M 1/02* (2013.01); *A01M 1/2055* (2013.01); *A61L 9/12* (2013.01); *B65D 83/00* (2013.01); *A61L 2209/133* (2013.01)

(58) Field of Classification Search
CPC ......... A01M 1/02; A01M 1/2055; A61L 9/12; A61L 9/04; A61L 2209/133; B65D 83/00
USPC .............. 239/34–60; D23/266, 368
See application file for complete search history.

(56) References Cited

U.S. PATENT DOCUMENTS

| | | | |
|---|---|---|---|
| 3,685,734 A | * 8/1972 | Paciorek | A61L 9/042 156/281 |
| 3,807,082 A | * 4/1974 | Hautmann | A61L 9/12 239/55 |
| D246,319 S | * 11/1977 | Rabussier | D23/369 |
| 4,155,500 A | 5/1979 | Dutcher | |
| D254,929 S | * 5/1980 | Butcher | D23/369 |
| 4,208,012 A | 6/1980 | Dutcher | |
| 4,277,024 A | * 7/1981 | Spector | A01M 29/12 206/466 |
| 4,305,892 A | * 12/1981 | Hallberg | F02M 7/106 261/36.2 |
| 4,306,892 A | * 12/1981 | Atalla | A61L 9/12 239/55 |
| D262,652 S | * 1/1982 | Jaeschke | D23/369 |
| 4,361,279 A | * 11/1982 | Beacham | A61L 9/12 239/56 |

(Continued)

FOREIGN PATENT DOCUMENTS

| | | |
|---|---|---|
| EP | 0697216 A2 | 2/1996 |
| EP | 1526770 | 9/2006 |

(Continued)

OTHER PUBLICATIONS

Alejandro L. Garcia, Physucs of Balance & Weight Shift, 2011, Creative Commons Attribution-Noncommerical-Share Alike 3.0, pp. 1-3, 7-8.*

(Continued)

*Primary Examiner* — Arthur O Hall
*Assistant Examiner* — Joseph A Greenlund (57) ABSTRACT

A passive volatile dispensing device includes a housing having first and second curved walls and sidewalls between the curved walls. A volatile-bearing substrate is disposed within an internal cavity of the housing. The first and second curved walls each include at least one aperture and at least two opposing sidewalls include a vent therein.

23 Claims, 7 Drawing Sheets

(56) References Cited

U.S. PATENT DOCUMENTS

| | | | |
|---|---|---|---|
| 4,660,763 A * | 4/1987 | Gutkowski | A61L 9/12 239/121 |
| 4,804,142 A * | 2/1989 | Riley | A01M 29/12 239/56 |
| 5,148,983 A * | 9/1992 | Muniz | B42D 15/045 239/34 |
| 5,304,358 A * | 4/1994 | Hoyt | A61L 9/12 239/56 |
| 5,460,787 A | 10/1995 | Colon | |
| 5,468,447 A * | 11/1995 | Bermas | A61L 9/01 422/1 |
| 5,547,636 A * | 8/1996 | Vick | A61L 9/042 239/60 |
| 5,704,832 A * | 1/1998 | Borrell | F24F 7/007 261/100 |
| 5,738,831 A | 4/1998 | Bethel | |
| 5,752,658 A * | 5/1998 | Gibbs | A61L 9/12 16/442 |
| 5,943,816 A * | 8/1999 | Hyatt | A01M 1/2005 239/34 |
| 6,327,813 B1 | 12/2001 | Ishiwatari | |
| 6,346,143 B1 * | 2/2002 | McGowan | A61L 9/12 96/117.5 |
| 6,386,971 B1 * | 5/2002 | Johnson | F24F 13/072 454/303 |
| D491,257 S * | 6/2004 | Picken, Jr. | D23/366 |
| 6,746,521 B2 * | 6/2004 | Canfield | A61L 9/12 239/56 |
| 6,899,281 B1 * | 5/2005 | Griese | D06F 58/203 239/60 |
| D508,285 S * | 8/2005 | Velicescu | D23/366 |
| D522,640 S * | 6/2006 | Miro | D23/366 |
| D544,590 S * | 6/2007 | Yoo | D23/351 |
| D551,333 S * | 9/2007 | Wu | D23/366 |
| D570,980 S * | 6/2008 | Isono | D23/366 |
| 7,380,370 B2 * | 6/2008 | Livingston | A01M 29/12 239/47 |
| 7,528,102 B2 | 5/2009 | Barthel et al. | |
| D613,391 S * | 4/2010 | Schwartz | D23/366 |
| D614,278 S * | 4/2010 | Schwartz | D23/366 |
| 7,770,817 B2 * | 8/2010 | Macor | A61L 9/04 206/0.5 |
| D646,769 S * | 10/2011 | Angel | D23/366 |
| D650,891 S * | 12/2011 | Freeborn | D23/366 |
| D662,251 S * | 6/2012 | Wauters | D26/85 |
| D666,284 S * | 8/2012 | Robinson | D23/368 |
| D673,666 S * | 1/2013 | Gordon | D23/366 |
| D675,307 S * | 1/2013 | Freeborn | D23/366 |
| 8,367,011 B2 * | 2/2013 | Yamamoto | A01M 1/2033 239/53 |
| D692,546 S * | 10/2013 | Gordon | D23/366 |
| 8,740,110 B2 * | 6/2014 | Gruenbacher | A61L 9/127 220/501 |
| 8,870,165 B2 * | 10/2014 | Scolari | A61L 9/122 239/58 |
| D723,150 S * | 2/2015 | Furner | D23/366 |
| 9,278,151 B2 * | 3/2016 | Westphal | A61L 9/12 |
| 2007/0075159 A1 * | 4/2007 | Lin | A61L 9/12 239/60 |
| 2008/0023568 A1 * | 1/2008 | Weggelaar | A61L 9/12 239/43 |
| 2011/0114663 A1 | 5/2011 | Brown et al. | |
| 2013/0056550 A1 * | 3/2013 | Zhang | A61L 9/12 239/59 |
| 2013/0175355 A1 * | 7/2013 | Lackey | A61L 9/12 239/57 |

FOREIGN PATENT DOCUMENTS

| | | |
|---|---|---|
| EP | 1526876 | 12/2006 |
| EP | 2569222 | 3/2013 |
| WO | 2004020004 | 3/2004 |
| WO | WO 2005087279 A1 | 9/2005 |
| WO | 2011140917 | 11/2011 |

OTHER PUBLICATIONS

Alejandro L. Garcia, Physics of Balance & Weight Shift, 2011, Creative Commons Attribution-Noncommericial-Share Alike 3.0, pp. 1-3, 7-8.*

PCT/US2014/051586 International Search Report and Written Opinion dated Mar. 3, 2015.

* cited by examiner

PASSIVE VOLATILE DISPENSING DEVICE

CROSS REFERENCE TO RELATED APPLICATIONS

Not applicable

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Invention

The present disclosure relates generally to a volatile material dispensing system and, more specifically, to a passive volatile material dispenser.

2. Description of the Background of the Invention

Passive volatile dispensing devices have become a long-established and popular means for releasing volatiles, such as insect repellents and fragrances, into the air. Common passive dispensers utilize a volatile-bearing material that is exposed to the surrounding atmosphere through vents on the housing. However, conventional passive dispensers tend to provide low release rates due to their configuration of apertures or grills that in effect trap the volatile inside the dispenser. For instance, typical passive dispensers comprise a perforated front and/or rear wall to promote emanation of the volatile from portions of the volatile-bearing material that are aligned with the perforations, such as a central region of the material. As such, conventional dispensers secure peripheral regions of the volatile-bearing material with flanges to allow airflow to reach the unobstructed central region of the material. However, such designs have poor volatile release rates due to a large quantity of the released volatile that becomes trapped within the housing and between the apertures. Even further, volatile release rates are greatly diminished at the peripheral regions of the volatile-bearing material due to obstruction of the housing flanges that cover the periphery of the material. Still further, common passive dispensers lack additional side vents that facilitate airflow through the sides of the housing to enhance diffusion and mitigate stagnant, trapped volatiles. As such, the low release rates reduce the distribution of the volatile and result in poor performance for the dispenser. Therefore, there is a need for a passive dispenser with improved airflow that does not trap the volatile inside.

Further, conventional passive dispensers are typically effective for a 1-2 month coverage period, whereupon the coverage becomes weak due, in part, to the dispenser design. As such, a user is required to replace the volatile-bearing material or purchase a new dispensing system. Frequent replacements are a nuisance to users who seek longer coverage periods, for instance, during mosquito season which typically lasts for four months. Therefore, there is a need for a slow, passive release dispenser that provides longer coverage periods and thus requires less frequent refills or replacements.

In addition, conventional passive dispensers appear functional and have limited options for deployment. For instance, the vents can be blocked if an upright passive dispenser is tipped over, thereby further reducing airflow and release of the volatile. There is a need for a more versatile passive dispenser that is operable in multiple positions, such as a dispenser that is mountable on a vertical or a horizontal surface. Even further, there is a need to provide a more aesthetically-pleasing dispenser that appears less functional, such that the dispenser is more "counter-worthy" and desirable to place in the open as opposed to the common utilitarian-style dispensers that are typically placed discretely. In fact, discrete placement of a passive dispenser may reduce its efficacy since it is blocked or hidden behind objects.

Therefore, there exists a need for an improved passive dispensing system. This invention is intended to address the above-noted needs and provide related advantages.

SUMMARY OF THE INVENTION

In one aspect of the present disclosure, a passive volatile dispensing device includes a housing having first and second curved walls and four sidewalls therebetween. A volatile-bearing substrate is disposed within an internal cavity of the housing. The first and second curved walls each include at least one aperture and at least two opposing sidewalls include a vent therein.

According to another aspect of the present disclosure, a passive volatile dispensing device includes a housing having first and second curved walls. The first and second curved walls define an internal cavity therebetween. First and second substrate-retaining ribs extend through the internal cavity from the first and second curved walls, respectively, which are configured to secure a non-peripheral region of a volatile-bearing substrate.

According to a different aspect of the present disclosure, a passive volatile dispensing device includes a housing having first and second curved walls. The first and second curved walls define an internal cavity therebetween for securing a volatile-bearing substrate therein. A central portion of at least one of the first and second curved walls has a surface area $B_A$ that is perforated to a lesser degree than that of a peripheral region surrounding the central portion.

DETAILED DESCRIPTION

FIGS. 1-11 show a volatile material dispensing system 100 that comprises a dispenser 102 with a volatile-bearing substrate 104 disposed therein. The dispenser 102 provides a curved, two-piece housing 106 that comprises a first wall 108 attached to a second wall 110 to define an internal cavity 112 therebetween. The first wall 108 is perforated with at least one aperture 114*a* and the second wall 110 is perforated with at least one aperture 114*b*. As illustrated in the present embodiment, a plurality of apertures 114*a, b* are provided on both of the first and second walls 108, 110 to release an active from the volatile-bearing substrate 104. The housing 106 further includes four sidewalls 116*a-d* that are traversed by a peripheral vent 118 extending 360 degrees circumferentially about the housing 106. As such, the housing 106 provides a cage-like chamber for releasing the active from the volatile-bearing substrate 104 through all of the first and second walls 108, 110 and the sidewalls 116*a-d* of the housing 106.

Figure 1:
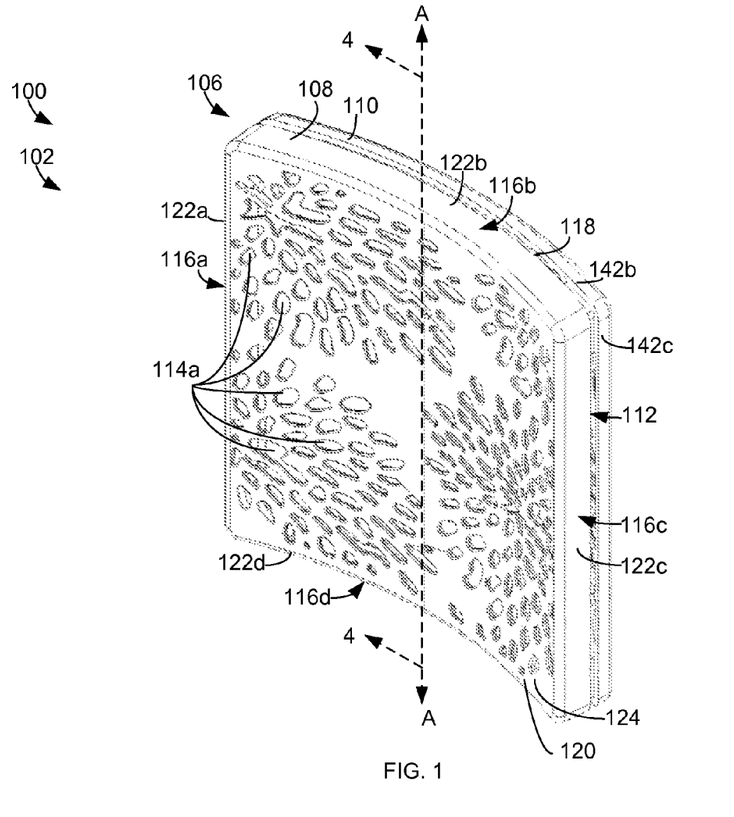
FIG. 1 is an isometric view of a volatile material dispenser.

As shown in FIGS. 1-7, the first and second walls 108, 110 are rectangular, arc-shaped walls that are complementary in shape, such that when the walls 108, 110 are attached, the housing 106 appears thin and curved. The thin profile appears minimal and lightweight, which is aesthetically appealing to consumers and requires less space than conventional passive dispensers that are more bulky. The curvature provides the top sidewall 116*b* and the bottom sidewall 116*d*, as shown in FIG. 1, with a relatively stable footprint for upright deployment of the dispenser 102 on a flat horizontal surface, such as a table-top. An added benefit of the curved profile is that the upright dispenser 102 can be tipped over on a flat resting surface and continue to release the active, since its curvature maintains at least a portion of the apertures 114*a, b* and the peripheral vent 118 about the sidewalls 116*a-d* above such a surface to allow for unobstructed airflow therethrough. As such, the dispenser 102 is operably deployable in numerous positions, such as upright, horizontal, or any angled position therebetween.

Still referring to FIGS. 1-7, the housing 106 is adapted to emanate the active from all sides including the sidewalls 116*a-d* by way of the peripheral vent 118. The peripheral vent 118 allows airflow to enter and exit through the housing 106 in addition to the air passageways provided by the apertures 114*a, b*. Further, the peripheral vent 118 facilitates emanation of the active from the edges of the volatile-bearing substrate 104 where a boundary layer of the flow past the substrate 104 is the thinnest. In particular, the boundary layer is a low energy, stationary layer of air near the surface of the volatile-bearing substrate 104 that the volatile must traverse in order to access the higher energy, moving air that carries it to the surroundings. The boundary layer increases in thickness moving inward from the edges toward a non-peripheral, central region C of the sheet-like volatile-bearing substrate 104, where the boundary layer increases to a thick stagnant layer of air. Since the active must travel through the stagnant layer to reach a higher flow region that dissipates the active to the surroundings, the emanation rate is typically lower toward the center and higher toward the edges of the volatile-bearing substrate 104. As such, the housing 106 is adapted to further promote diffusion from the edges of the volatile-bearing substrate 104 by minimizing obstructions thereto, for instance, by securing the substrate primarily at non-peripheral regions thereof and utilizing minimal edge securing contacts, as described further below.

Further, the housing 106 is adapted to receive airflow directed into the first and second walls 108, 110 and through the volatile-bearing substrate 104, as well as to direct airflow through the housing 106 along the curvature of the walls 108, 110 and the substrate 104 by way of the peripheral vent 118. It is contemplated that the airflow traveling along the curved volatile-bearing substrate 104, rather than directly through the thickness of the substrate 104, may pick up a higher concentration of volatiles due to its prolonged travel across the substrate 104. As such, airflow leaving the sidewalls 116*a-d* may carry a higher concentration of volatiles for release than airflow directed from the apertures 114*a, b* of the first and second walls 108, 110. In a particular aspect, a non-peripheral region of the housing 106 is solid and non-perforated to further guide the airflow through the curvature of the housing 106 and prevent the airflow from prematurely escaping through the apertures 114*a, b* before reaching the sidewalls 116*a-d*. Further, the peripheral vent 118 promotes emanation from the edges of the volatile-bearing substrate 104, where the boundary layer is thinnest and thus the emanation rate is highest. When the active in the edge regions have been depleted, the central region of the volatile-bearing substrate 104 continues to slowly release the active by airflow that is carried through the housing from the sidewalls 116*a-d*.

Referring to FIGS. 2, 4, and 5, the volatile-bearing substrate 104 disposed within the dispenser 102 is a cellulosic substrate that is impregnated with and/or coated with an active ingredient for diffusion into the surrounding atmosphere, such as a pest control active, insect repellent, fragrance, air freshener, or odor eliminator. It is contemplated that the cellulosic material is a paper-like plaquette about 3 in. (76.2 mm) tall by about 3 in. (76.2 mm) wide. In one preferred embodiment, the material is a thin sheet of material that is at least about 50 mm tall by about 50 mm wide; in a more preferred embodiment, the plaquette is flexible and at least about 60 mm tall by about 60 mm wide; in a most preferred embodiment, the material is at least about 75 mm tall by about 75 mm wide and adapted to substantially occupy the internal cavity 112 of the housing 106. In fact, the substrate and housing may comprise any shape or size. For example, in another embodiment the plaquette is larger and has dimensions of about 279 mm tall by about 216 mm wide and the housing 106 is sized or shaped accordingly to fully receive the plaquette therein. For instance, the size of the housing 106 can be increased to between about 279 mm tall to about 300 mm tall by about 216 mm to wide to about 230 mm wide such that it is rectangular shaped and adapted to receive the larger, rectangular-shaped plaquette, In another embodiment, the larger plaquette and/or accommodating housing 106 is about 254 mm tall by about 152 mm wide. In a different embodiment, the larger plaquette is about 127 mm tall by about 177 mm wide. Further, it is contemplated that the material may comprise any dimensions in height, width, and thickness that are similar to the dimensions of the housing 106. The volatile-bearing substrate 104 preferably has a paper-thin thickness and is impregnated to provide an effective coverage area of approximately 20 cubic meters surrounding the substrate 104 when diffused from the dispenser 102. It is further contemplated that the volatile-bearing substrate 104 can be flexible, rigid, and/or pre-curved to conform to the curvature of the arc-shaped housing 106. Further, it is noted that multiple volatile-bearing substrates 104 can be disposed within the dispenser 102 simultaneously. The multiple volatile-bearing substrates 104 may be separate, attached or integrally formed together, or may comprise a large substrate 104 imparted with one or more fold lines such that the substrate 104 is folded when received into the dispenser 102.

In one embodiment, the active ingredient in the volatile-bearing substrate 104 is preferably an insecticide, an insect repellant, or an insect attractant. Alternatively, the active ingredient may be a disinfectant, sanitizer, air purifier, aromatherapy scent, antiseptic, air-freshener, and/or deodorizer. Other examples of active ingredients include fragrances (e.g., natural and synthetic oils), odor eliminators, such as triethyleneglycol and/or propylene glycol, antimicrobials, anti-bacterials, corrosion inhibitors, pH adjustors, preservatives, organic acids, and the like, or any other active ingredient(s) that are usefully dispersed into the air.

In one embodiment, the active ingredient is an insecticide and/or insect repellent, an organic phosphorous insecticide, a lipidamide insecticide, a natural repellent such as citronella oil, a natural pyrethrin, a pyrethrum extract, or a synthetic pyrethroids. Suitable synthetic pyrethroids are acrinathrin, allethrin as D-allethrin, Pynamin®, benfluthrin, bifenthrin, bioallethrin as Pynamin Forte®, S-bioallethrin, esbiothrin, esbiol, bisoresmethrin, cycloprothrin, cyfluthrin, beta-cyfluthrin, cyhalothrin, lambda-cyhalothrin, cypermethrin, alpha-cypermethrin, beta-cypermethrin, cyphenothrin, deltamethrin, empenthrin, esfenvalerate, fenpropathrin, fenvalerate, flucythrinate, taufluvalinate, kadethrin, permethrin, phenothrin, prallethrin as Etoc®, resmethrin, tefluthrin, tetramethrin, tralomethrin, metofluthrin, transfluthrin, and/or combinations thereof. In alternative versions, the volatile insecticide is selected from the group consisting of transfluthrin, metofluthrin, vapothrin, permethrin, prallethrin, tefluthrin, and esbiothrin. In a particular embodiment, the volatile-bearing substrate 104 is a sheet of cellulosic material treated with transfluthrin, an insect repellant, and Proglyde™ DMM, a solvent.

Further, a wide variety of volatile fragrances may be used that may optionally also have insect control attributes. Alternatively, some fragrances may be selected that provide a deodorizing function (e.g., certain terpenes). Still further, various natural and artificial perfumes may be used. Non-limiting examples of these perfumes include animal-based and plant-based natural perfumes, and artificial perfumes such as alcohols, phenols, aldehydes, ketones, terpenes, and esters.

The fragrance according to this disclosure may comprise one or more fragrant materials or materials that provide chemically active vapors. In one embodiment, the fragrance can comprise and/or include volatile, fragrant compounds including, but not limited to natural botanic extracts, essences, fragrance oils, and so forth. As is known in the art, many essential oils and other natural plant derivatives contain large percentages of highly volatile scents. In this regard, numerous essential oils, essences, and scented concentrates are commonly available from companies in the fragrance and food businesses.

Exemplary oils and extracts include, but are not limited to, those derived from the following plants: almond, amyris, anise, armoise, bergamot, cabreuva, calendula, canaga, cedar, chamomile, coconut, eucalyptus, fennel, jasmine, juniper, lavender, lemon, lemongrass, orange, palm, peppermint, quassia, rosemary, thyme, and so forth.

Figure 5:
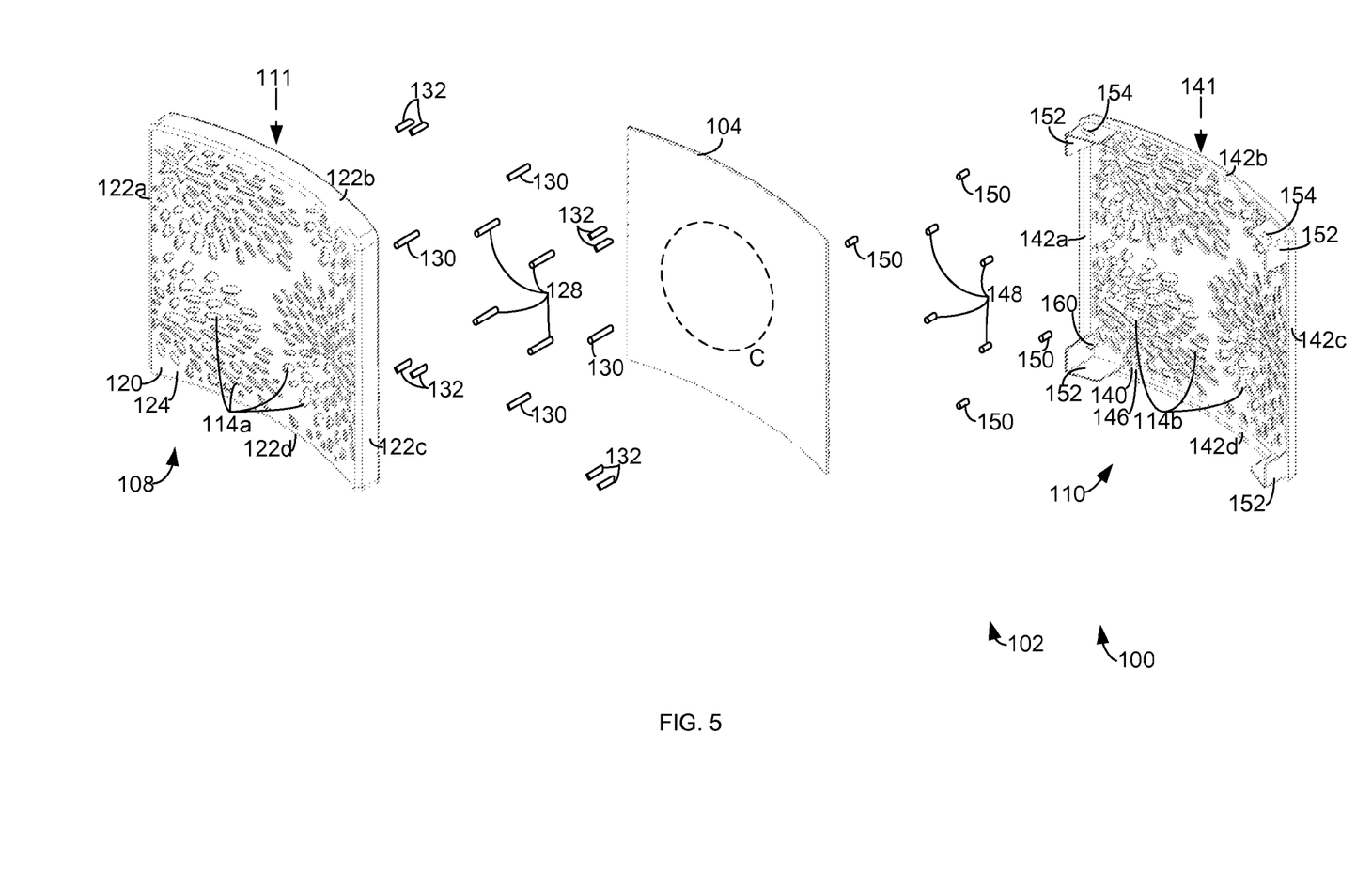
FIG. 5 is an exploded isometric view of the volatile material dispenser of FIG. 1.
Figure 7:
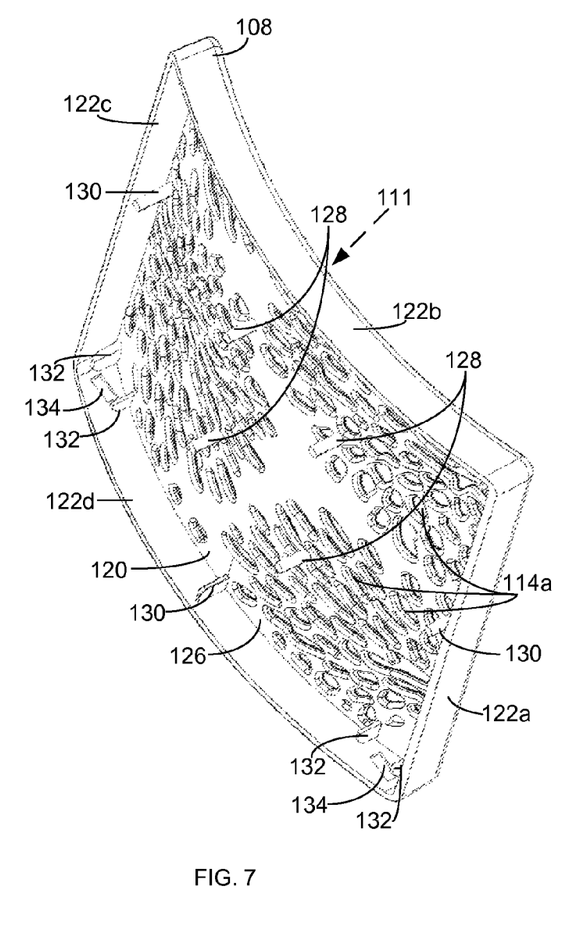
FIG. 7 is an angled view of a second wall of the volatile material dispenser of FIG. 1.

Referring to FIGS. 1, 5, and 7, the first wall 108 of the dispenser 102 comprises a curved first plate 120 bounded on its four edges by four side panels 122a-d that extend transversely toward the second wall 110. In the particular embodiment shown in FIG. 1, the curved first plate 120 is generally square-shaped and arced with an apex 111 extending toward the internal cavity 112. The two opposing side panels 122a, c are rectangular-shaped and the remaining opposing side panels 122b, d are curved. The side panels 122a-d form a portion of the sidewalls 116a-d on the housing 106. The curved first plate 120 is perforated by a plurality of apertures 114a that traverse through the thickness of the plate 120. It is contemplated that the first plate 120 has a uniform thickness ranging from about 0.01 mm to about 0.5 mm that extends between an external surface 124 of the housing 106 to an internal surface 126 thereof. It is further contemplated that the first wall 108 and any other components of the housing 106 are formed from injection molded plastic, e.g., polypropylene, or formed from other materials, such as metal, glass, paperboard, co-polyester resins, nylon, and other materials, or any combination thereof.

Figure 4:
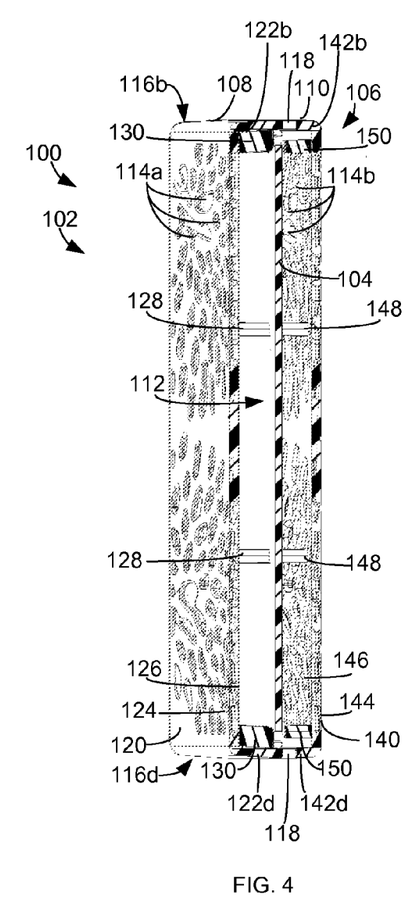
FIG. 4 is a sectional view of the volatile material dispenser of FIG. 1 generally taken along line 4-4 thereof.

Referring to FIGS. 4, 5, and 7, the internal surface 126 of the first wall 108 has at least one substrate-retaining rib 128 adapted to extend through the internal cavity 112 and engage the central region C of the volatile-bearing substrate 104. It is noted that the central region C shown in FIG. 5 is an imaginary boundary projected onto the surface of the volatile-bearing substrate 104 for purposes of discussion only. In an aspect, securing the central region C of the volatile-bearing substrate 104 promotes emanation of the active by preserving the generally unobstructed peripheral regions of the substrate 104 where the boundary layer is thinnest and the emanation rate is highest. In the particular embodiment shown in FIG. 5, four substrate-retaining ribs 128 extend from a non-peripheral region of the internal surface 126, such as a central region of the internal surface 126. The substrate-retaining ribs 128 are upstanding posts that are spaced apart about the central region in order to impart a curvature on the central region C of the volatile-bearing substrate 104. In the particular embodiment as shown in FIG. 4, the substrate-retaining ribs 128 further align with corresponding substrate-retaining ribs 148 provided on the second curved wall 110. It is contemplated that the substrate-retaining ribs 128, 148 can also be misaligned in the non-peripheral region of the first and second walls 108, 110 to impart a curvature on the volatile-bearing substrate 104. The length of each substrate-retaining rib 128 is approximately the same height as the side panels 122a-d to sufficiently space the volatile-bearing substrate 104 away from the curved first plate 120 and closer to level with the peripheral vent 118. The substrate-retaining ribs 128 also prevent the inserted volatile-bearing substrate 104 from sitting too far into the first wall 108. In another aspect, the substrate-retaining ribs 128, 148 offset the edge of the volatile-bearing substrate 104 from the peripheral vent 118 to discourage unintended removal or access to the substrate 104. It is noted that any features of the substrate-retaining ribs 128 or any other component discussed herein, such as arrangement and geometry, are not intended to limit such aspects of the present invention.

As further shown in FIGS. 4, 5, and 7, the first wall 108 further provides at least one peripheral rib 130 extending from the peripheral region of the internal surface 126. Merely by way of example in FIG. 5, four peripheral ribs 130 are provided along the edges of the internal surface 126 generally about a centerpoint of each edge, such that a single peripheral rib 130 is provided adjacent to a centerpoint of each side panel 122a-d. It is contemplated that the peripheral ribs 130 further secure and/or impart a curvature on the volatile-bearing substrate 104 when aligned with a set of corresponding peripheral ribs 150 provided on the second curved wall 110, as described below. Further, it is contemplated that the peripheral ribs 130, 150 can also be misaligned about the peripheral region of the first and second walls 108, 110 to retain and/or impart a curvature on the volatile-bearing substrate 104. In an aspect, each peripheral rib 130 engages an edge of the sheet-like volatile-bearing substrate 104, as shown in FIG. 4, to align the edge of the substrate 104 with the peripheral vent 118 and thereby enhance emanation at the edges. The peripheral ribs 130 further ensure that an adequate gap exists between the volatile-bearing substrate 104 and the internal surface 126. It is noted that while any number of peripheral ribs 130 can be contemplated, preferably a range of about 1 to about 12 peripheral ribs 130 is distributed about the first wall 108 so as not to obstruct the peripheral region of the volatile-bearing substrate 104. Further, it is contemplated that the peripheral ribs 130 are formed similar to the substrate-retaining ribs 128 discussed above, although other shapes and sizes can be contemplated. For example, as shown in FIGS. 5 and 7, the two opposing peripheral ribs 130 adjacent to the two opposing curved side panels 122*b, d* are flat, slab-like projections as opposed to being circular post-like structures, such as those used with other peripheral ribs 130. Alternatively, it is contemplated that all of the peripheral ribs 130 are circular, post-like structures or all are flat, slab-like projections, or any combination thereof. Further, it is contemplated that any or all of the peripheral ribs 130 can be formed integrally with the side panels 122*a-d* and/or the curved first wall 108.

Figure 9:
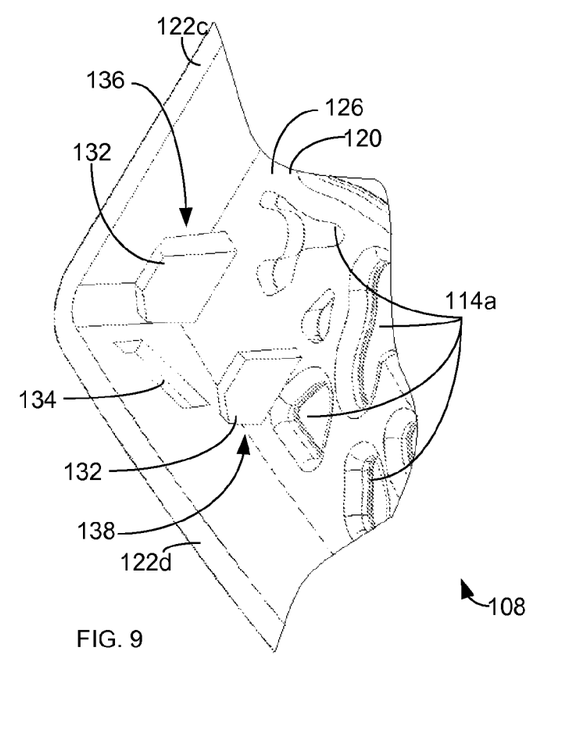
FIG. 9 is a close-up view of a corner of the second wall shown in FIG. 7.

Referring to FIGS. 5 and 9, the first wall 108 is adapted to snap-lock to the second wall 110 at the four corners of the walls 108, 110. Each corner of the first wall 108 includes a projecting pair of snap-lock ribs 132, for a total of eight snap-lock ribs on the first wall 108. The snap-lock ribs 132 are flat, slab-like projections disposed in parallel and are spaced apart about 0.1 cm to about 1.0 cm between each rib 132 pairing. A longitudinal groove 134 is provided along a portion of the sidewalls 122*b, d* on an inner surface that spans the spacing of each rib 132 pairing. It is contemplated that the longitudinal groove 134 does not extend through the thickness of the sidewall 122*a-d* so as to minimize accessibility of the snap-lock mechanism from outside of the housing 106, and thereby prevent tampering and un-locking of the housing 106. Further, each pair of snap-lock ribs 132 defines a slot 136 and a slot 138. As demonstrated in FIG. 9, the slot 136 extends as a gap between one snap-lock rib 132 and its adjacent, parallel side panel 122*c*. The slot 138 extends as a gap about both snap-lock ribs 132 of the rib pair and its adjacent, transverse side panel 122*d* that provides the longitudinal groove 134. As such, each snap-lock rib 132 pair defines two slots 136, 138 between the surrounding side panels 122*c, d*, whereby the slots 136, 138 are configured to receive corresponding snap-lock elements provided on the second wall 110, as discussed below. It is noted that at least one corner of the first wall 108, and preferably all four corners, are constructed in a similar fashion to snap-lock engage the second wall 110. Further, it is noted that other housing supports or locking mechanisms can be contemplated for securing the first and second walls 108, 110 together as would be known to those of ordinary skill in the art, e.g., latches, interference fits, grooves with corresponding nubs or projections, adhesives, etc.

Figure 6:
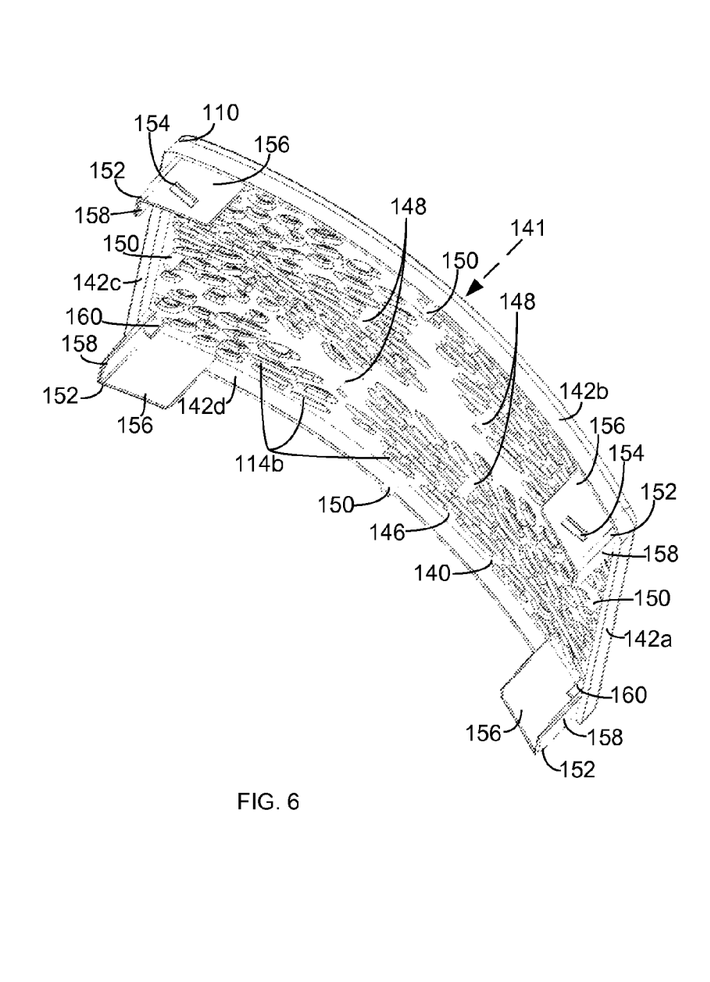
FIG. 6 is an angled view of a first wall of the volatile material dispenser of FIG. 1.

Turning to FIGS. 1, 5, and 6, the second wall 110 of the dispenser 102 is configured in a similar fashion to the first wall 108 described above, except for the differences noted herein. The second wall 110 comprises a curved second plate 140 bounded on its four edges by four side panels 142*a-d* that extend transversely toward the side panels 122*a-d* of the first wall 108. In the particular embodiment shown in FIG. 5, the curved second plate 140 is generally square-shaped and arced away from the internal cavity 112, whereby an apex 141 of the arc extends away from the internal cavity 112. As such, the second plate 140 is concave away from the internal cavity 112, while the complementary first plate 120 is convex into the cavity 112, whereby the apex 111 of the first plate 120 extends into the cavity 112. The two opposing side panels 142*a, c* are rectangular-shaped and the remaining two side panels 142*b, d* are curved. The side panels 142*a-d* are shallower in width than the side panels 122*a-d* such that the panels 122*a-d*, 142*a-d* collectively form the sidewalls 116*a-d* of the housing 106. The curved second plate 140 is perforated with a plurality of apertures 114*b* that extend through the thickness of the plate 140, which may have a uniform thickness ranging from about 0.01 mm to about 0.5 mm that extends between an external surface 144 of the housing 106 to an internal surface 146 thereof. In the present embodiment, the apertures 114*a, b* on the first and second walls 108, 110 are mirrored on both sides of the housing 106. However, it is contemplated that the apertures 114*a, b* can be different on the first and second walls 108, 110 to generate different aesthetic designs and/or flow patterns, as described below.

Referring to FIGS. 4, 5, and 6, the internal surface 146 of the second wall 110 provides at least one substrate-retaining rib 148 adapted to extend through the internal cavity 112 and engage the central region C of the volatile-bearing substrate 104. In particular, four substrate-retaining ribs 148 extend from a central region of the internal surface 146 to align with the four substrate-retaining ribs 128 provided on the first wall 108. The substrate-retaining ribs 128, 148 impart a bending force on the flexible, sheet-like volatile-bearing substrate 104 to curve the substrate 104 in a complementary manner to the arc of the first and second walls 108, 110. It is contemplated that the length of each substrate-retaining rib 148 on the second wall 110 is approximately the same height as the side panels 142*a-d* to sufficiently space the volatile-bearing substrate 104 away from the curved second plate 140 and closer to level with the peripheral vent 118. As such, the substrate-retaining ribs 148 are more shallow than the substrate-retaining ribs 128. The substrate-retaining ribs 148 also prevent the inserted volatile-bearing substrate 104 from sitting too far into the second wall 110. It is contemplated that the substrate-retaining ribs 148 can be aligned or misaligned with the substrate-retaining ribs 128 provided on the first plate 108.

In a particular aspect, the volatile-bearing substrate 104 is sandwiched between the corresponding substrate-retaining ribs 128, 148 when the ribs 128, 148 are aligned. The substrate-retaining ribs 128, 148 can be aligned with no space therebetween and thereby fixedly pinch portions of the volatile-bearing substrate 104 retained therein. In another embodiment, the substrate-retaining ribs 128, 148 can be aligned yet spaced apart to define a gap to accommodate different thicknesses or changing shapes of the volatile-bearing substrate 104. In fact, the spacing may be adapted to provide a relatively tight fit for any sized volatile-bearing substrate 104 so that the substrate 104 is substantially immovable, i.e., the substrate-retaining ribs 128, 148 may pierce, squeeze, or be sized to touch a surface of the substrate 104 to substantially prevent movement. In other embodiments, a slight gap may be provided to allow for minimal or substantial movement of the volatile-bearing substrate 104, or to allow for changing surface characteristics of the substrate 104, e.g., a substrate 104 that increases or decreases its thickness over time as the volatile is diffused. For instance, it is contemplated that the volatile-bearing substrate 104 contacts the substrate-retaining ribs 128 at a beginning of the coverage period, and bends after exposure to the atmosphere toward the end of the coverage period to contact the substrate-retaining ribs 148. In this case, the spaced-apart substrate-retaining ribs 128, 148 more freely secure the volatile-bearing substrate 104 to allow for changing shapes of the substrate 104 without distorting the housing 106. Further, the substrate-retaining ribs 128, 148 can be misaligned and/or offset in order to define a gap for receiving the volatile-bearing substrate 104. Further, it is contemplated that the spaced apart substrate-retaining ribs 128, 148 may accommodate a plurality of volatile-bearing substrates 104 to be secured therein in any of the manners discussed above. In one embodiment, the gap between the substrate-retaining ribs 128, 148 is between about 0 cm to about 1 cm, and more preferably about 0.1 cm to about 0.5 cm. It is noted, however, that the range of the gap provided herein is non-limiting and that other ranges are contemplated.

As further shown in FIGS. 4, 5, and 6, the second wall 110 further provides at least one peripheral rib 150 depending from a peripheral region of the internal surface 146. In the embodiment shown in FIG. 5, four peripheral ribs 150 are provided such that a single peripheral rib 150 is provided adjacent to a centerpoint of each second side panel 142a-d. The peripheral ribs 130 on the first wall 108 are configured to align with the peripheral ribs 150 on the second wall 110 to secure the volatile-bearing substrate 104 and optionally impart a curvature thereon. As such, the peripheral ribs 130, 150 retain the volatile-bearing substrate 104 within the internal cavity 112 of the housing 106. It is contemplated that the peripheral ribs 130, 150 can be aligned together or misaligned. Further, it is contemplated that the volatile-bearing substrate 104 can be fixedly or more freely retained between the peripheral ribs 130, 150 in a similar fashion to the substrate-retaining ribs 128, 148 described above.

Figure 8:
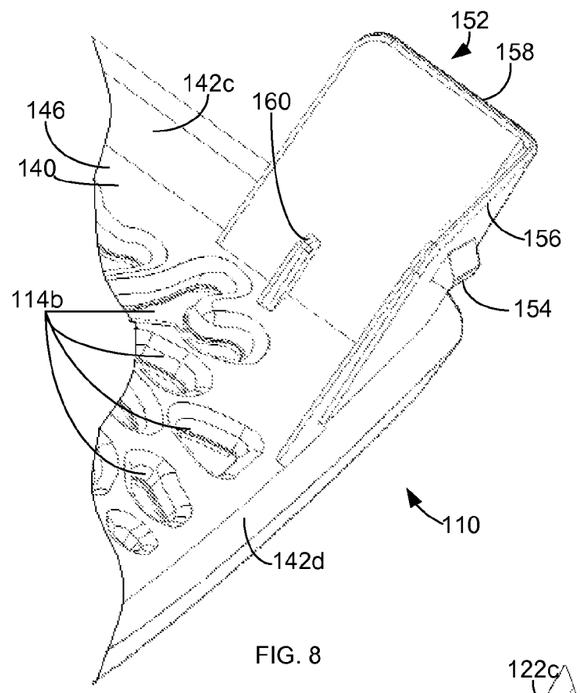
FIG. 8 is a close-up view of a corner of the first wall shown in FIG. 6.

Referring to FIGS. 5 and 8, the second wall 110 is adapted to snap-lock to the first wall 108 at the four corners of the walls 108, 110. Each corner of the second wall 110 includes a snap-lock bracket 152 for a total of four brackets extending from the internal surface 146. The snap-lock brackets 152 may be formed integrally with the internal surface 146 and/or their respective, adjacent side panels 142a-d. As shown in FIG. 8, each snap-lock bracket 152 includes a single longitudinal peg 154 that is configured to catch the corresponding longitudinal groove 134 provided on the first side panels 122b, d. The longitudinal peg 154 projects from a tab 156 disposed substantially transverse to the rectangular sidewalls 142a and 142c. A tab 158 is disposed substantially parallel to the rectangular sidewalls 142a and 142c and is connected to the tab 156. It is contemplated that the snap-lock brackets 152 are formed in complementary shape to a portion of the first and second walls 108, 110, which may be a substantially right-angled corner or any other geometry. In operation, the tab 158 and the tab 156 are inserted into the corresponding slot 136 and the slot 138, respectively, provided on the first wall 108 as shown in FIG. 9. The snap-lock ribs 132 on the first wall 108 that define the slots 136, 138 prevent the tabs 156, 158 from flexing, backing out, or coming unlatched. As such, the snap-lock mechanism is intended to inseparably join the corner, peripheral regions of the first wall 108 and the second wall 110 to prevent a user from accessing the volatile-bearing substrate 104. Further, as shown in FIG. 8, one or more bracket supports 160 are integrally formed with each snap-lock bracket 152 and the internal surface 146 adjacent thereto for additional structural integrity.

As shown in FIGS. 1-4, in operation the first and second walls 108, 110 are snap-locked with complementary curvature to form the two-piece housing 106, whereby the side panels 122a-d and the opposing side panels 142a-d collectively form the four sidewalls 116a-d of the housing 106. In particular, the housing 106 is generally an arc-shaped rectangular cage with four sidewalls 116a-d. The snap-lock mechanism, and in particular the geometric depth of the snap-lock brackets 152 projecting from the second plate 140, provides adequate spacing to define the peripheral vent 118 that circumnavigates the housing 106 between the opposing side panels 122a-d and 142a-d. In an alternative embodiment, the snap-lock ribs 128, 148 are adapted to space the opposing side panels 122a-d and 142a-d in order to define the peripheral vent 118. Further, it is anticipated that other structures alone or in combination with the aforementioned elements may be used to create a gap or space between the first and second walls 108, 110. In the present embodiment, the peripheral vent 118 extends around the entire housing 106. Further, it is contemplated that in another embodiment that the peripheral vent 118 extends around substantially all of the housing 106, or more than about 90 percent of the housing 106, or alternatively, more than 75 percent of the housing 106, or further alternatively, more than 50 percent of the housing 106. Further, it is preferred that the peripheral vent 118 be provided with a substantially uninterrupted pathway through the housing 106 to allow air flow access to the volatile-bearing substrate 104. However, in some embodiments, corners of the housing 106 may include structure that impedes air flow through the peripheral vent 118, or other peripheral portions may impede air flow. It is desirable to minimize such impediments, so that preferably about 80 percent or more of the peripheral vent 118 is uninterrupted, or about 60 percent of the peripheral vent 118 is uninterrupted, or 40 percent or more of the peripheral vent 118 is uninterrupted. Merely by way of example, it is contemplated that the peripheral vent 118 is a gap of uniform width between about 1 mm to about 10 mm, and preferably between about 3 mm to about 5 mm, and most preferably about 3 mm. In a different embodiment, the peripheral vent 118 is between about 12 mm to about 50 mm. It is also contemplated that any of the vents may have varying widths throughout a length of the sidewalls 116a-d or on differing sidewalls. For instance, it is contemplated that the peripheral vent 118 may be about 25 mm wide on at least two of the four sidewalls 116a-d and about 43 mm wide on one additional sidewall 116a-d, which operates as a top sidewall when deployed. It is noted, however, that other configurations can be contemplated, including a plurality of peripheral vents 118 disposed on one or more sidewalls 116a-d. In a different configuration, the plurality of peripheral vents 118 are orifices that are perforated in one or more side panels 112a-d and 142a-d, whereby the side panels 112a-d and 142a-d extend toward each other to form a space or no space therebetween. Further, it is contemplated that at least one sidewall 116a-d provides a peripheral vent 118, and preferably at least two opposing sidewalls 116a-d include peripheral vents 118 disposed thereon.

Figure 2:
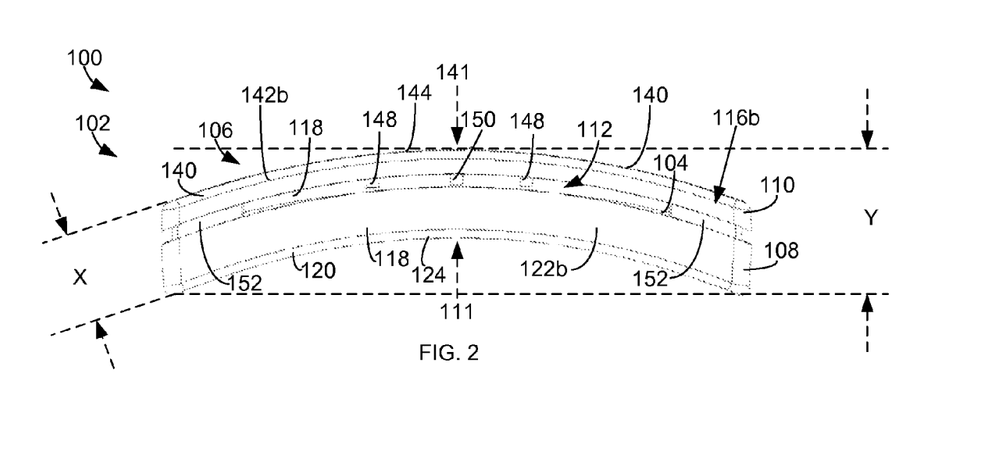
FIG. 2 is a top elevational view of the volatile material dispenser of FIG. 1 and further provides a mirror image of a bottom elevational view thereof.
Figure 3:
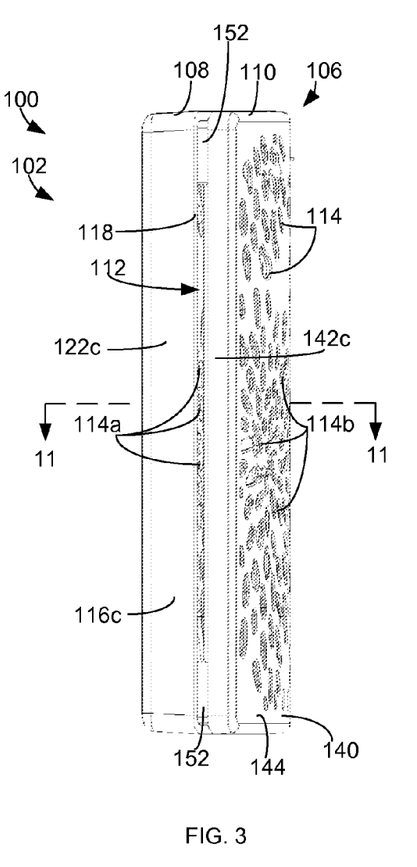
FIG. 3 is a side elevational view of the volatile material dispenser of FIG. 1.

Further, as shown in FIGS. 1 and 2, it is contemplated that the first and second walls 108, 110 define an arcuate sidewall 116b having a sidewall width x and a footprint width y such that y/x is a constant. In FIGS. 1 and 2, each sidewall 116 comprises a uniform, thin width x and two opposing arcuate sidewalls 116b, d that yield a footprint width y, whereby y=1.85*x and 1.85 is a constant. Merely by way of example, the sidewall width x is about 1.40 mm and the footprint width y is about 2.59 mm. It is contemplated that the footprint width y is adequate for assisting a stable, upright deployment of the dispenser 102 on a flat, horizontal surface, such as a table-top. As such, other constants may be used generate the arc profile that assists in upright deployment. Preferably, the constant is between about 1.5 to about 2.5, and most preferably the constant is between about 1.75 to about 2. Further, the housing 106 may be configured to incorporate other deployment structures, including magnetic elements for adhering to magnetic surfaces, removable clips, stands, and the like.

Figure 10:
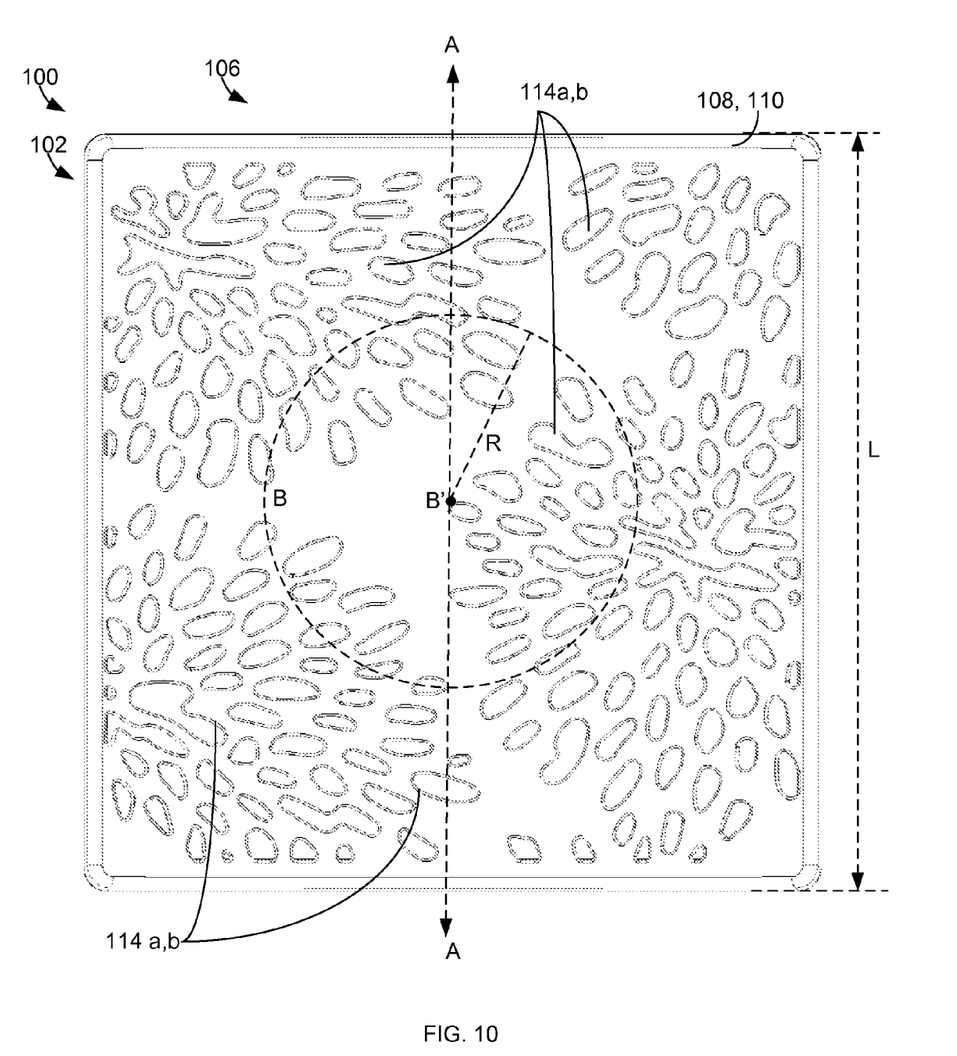
FIG. 10 is a front view of a first or second wall of the volatile material dispenser of FIG. 1.

As shown in FIGS. 1 and 10, the two-piece housing 106 defines a central inflection line A shown projected through the crest or trough of the housing 106 as delineated by the apexes 111, 143 of the first and second plates 120, 140, respectively. It is contemplated that a pattern of the apertures 114a, b provided on the first wall 108, second wall 110, or both, includes a higher concentration of apertures 114a, b about the peripheral portions of the walls 108, 110 surrounding a non-peripheral region, such as a central region B of the walls 108, 110. The central region B includes a centerpoint B' aligned with the central inflection line A. Merely by way of example, the central region B defines a radius R that is about ¼ the length L of one side of the square-shaped housing 106. The central region B generally overlaps with the central region C of the volatile-bearing substrate 104 disposed behind the wall 108, 110. Preferably, greater than 75 percent of the peripheral portion of the wall 108, 110 surrounding the central region B is open, while about 0 percent to about 75 percent of the central region B is open. More preferably, about 15 percent to about 50 percent of region B is open. Most preferably, less than about 50 percent of the central region B is open, and more preferably about 25 percent or less is open. As such, the central region B generally comprises a solid, non-perforated portion that may be irregularly shaped due to the distribution of the apertures 114a, b therein, as illustrated by the amorphous solid portion of the central region B in FIG. 10. Further, it is noted that the first and second walls 108, 110 can have different percentages of open areas in the peripheral portion and the non-peripheral, central region B.

In a particular aspect, the area of the non-peripheral, central region B is characterized by a ratio of its surface area $B_A$ to a surface area $S_A$ of a face of the housing 106 on which the central region B is disposed. For instance, as shown in FIG. 10, the central region B comprises a surface area that is inclusive of both solid and perforated portions bound therein, such that the entire region covers approximately 75 percent or less of the surface area of the first and second wall 108, 110 that it is disposed on. Preferably, a percentage of the central region B to the surface area of the wall 108, 110 is between about 10 percent to about 50 percent; more preferably, the percentage of the central region B to the surface area of the wall 108, 110 is about 15 percent to about 40 percent; most preferably, the percentage is about 25 percent of the total surface area of wall 108, 110. Thus, merely by way of example for a preferred ratio, the size of central region B is characterized by the formula $B_A=0.25*S_A$. This characterization of the central region B can be manipulated to apply various configurations to the housing 106 that define a variety of shapes, such as stars, triangles, circles, and other geometric configurations.

It is further contemplated that the ratio of the surface area $B_A$ of the central region B to the total surface area $S_A$ of the included first and second wall 108, 110 is further defined in conjunction with the curvature of the housing 106. For instance, it is contemplated that the first wall 108, which curves inwardly into the volatile-bearing substrate 104 disposed therein, guides airflow entering from a sidewall 116a, c by providing a covered passageway particularly in the non-peripheral or central portion of the first wall 108. For instance, the change in direction of the airflow across the arced volatile-bearing substrate 104 may rebound or redirect the air flow away from the substrate 104 and out of the apertures 114a located more centrally on the first wall 108. As such, the solid central region prohibits significant premature escape of airflow by bounding the airflow inside the housing 102. Similarly, with respect to the second wall 110 that curves outwardly away from the volatile-bearing substrate 104, any throughflow of air that tends to project away from the crest of the arced substrate 104 is bounded back into the housing 102 by the less perforated central region B of the second wall 110. As such, the central region B disposed on either or both of the first and second walls 108, 110 provides an airflow passageway through the housing 102. Therefore, the central region B is further sized to capture or otherwise redirect any airflow that may be deflected due to the arc-shaped housing 102.

Figure 11:
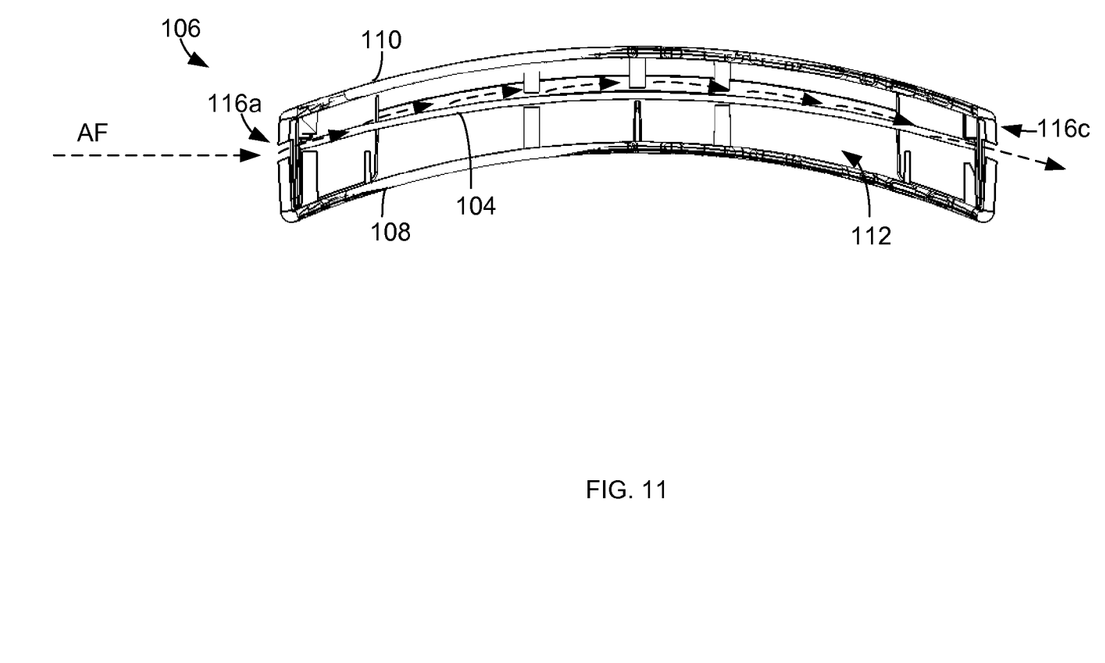
FIG. 11 is a top cross-sectional view of airflow through the volatile material dispenser of FIG. 1 generally taken along the line 11-11 of FIG. 3.

Turning to FIG. 11, it is contemplated that providing a solid, central region guides airflow from the peripheral vents 118 through the internal cavity 112 of the dispenser 102. In particular, the generally solid center guides the airflow toward the peripheral regions of the volatile-bearing substrate 104 to maximize emanation of the active closer to the edges of the substrate 104. In particular, FIG. 11 illustrates airflow AF directed into the sidewall 116a and guided through the internal cavity 112 of the housing 106 to exit the opposing sidewall 116c thereof. It is noted that the airflow AF can be guided between the volatile-bearing substrate 104 and the second wall 110, and/or the substrate 104 and the first wall 108. Further, the airflow AF can escape through any of the remaining sidewalls 116b, d that are unobstructed during deployment. In fact, the airflow AF is substantially dependent on the ambient condition in the room or environment the housing 106 is provided in. However, it has been found that the present configuration allows for increasing efficient diffusion of volatile when the airflow AF is directed through opposing sides of the housing 106. Such a structure provides significant advantages over prior art dispensers that only allow for airflow through first and second faces of the dispenser.

In one particular embodiment shown in FIG. 10, the length L of the housing 106 is about 7.6 cm and is uniform about all four sides of the housing 106 to define an area of about 58 cm$^2$. The pattern of apertures 114a, b provides a total open area of about 6 in$^2$ (38.7 cm$^2$), whereby the concentration of apertures 114a, b increases away from a central region of the first or second wall 108, 110. In an aspect, the apertures 114a, b include generally irregularly shaped holes of non-uniform shapes and sizes. It is contemplated that the patterns on the first and second walls 108, 110 are mirrored on both sides of the housing 106, although other patterns can be contemplated for one or both of the walls 108, 110, including a plurality of horizontal grills, curved lines, or other geometries. For instance, certain patterns such as soft curves, radii, blossom patterns, and other natural shapes may be formed by the apertures 114a, b to improve the feel and tone delivered in viewing the dispenser 102. Further, it is contemplated that the first and second sides of the housing 106 have different designs of apertures 114a, b to provide different looks and feels for the user to selectively display. Merely by way of example, the first wall 108 can have apertures 114a designed with summer motifs while the second wall 110 provides apertures 114b designed with autumnal themes to provide the user with different display themes that transition through the seasons. Even further, it is noted that the concentration of apertures 114a, b may be different between the first and second walls 108, 110.

In practice, a set of directions for use of the dispensing system 100 may be provided to the user on an accompanying label, insert, or packaging of the system 100. The directions may include, in part, recommended uses of the dispensing system 100 and effective coverage periods and ranges. For instance, the directions may instruct the user to remove the dispensing system 100 from its packaging, such as an air-tight pouch, and place the dispensing system 100 in a room of approximately 8 m². The directions may also suggest that if a larger area of protection is required, such as up to approximately 17 m², placing an additional dispensing system 100 in the room, such as across the room from the first dispensing system 100, may be desirable.

Further, the directions may recommend placement configurations for maximizing effectiveness of the dispensing system 100. Merely by way of example, the directions may suggest placing the dispensing system 100 above floor level and away from walls; placing the system 100 at least a meter away from any other surface; avoiding placement in direct sunlight or near open windows; placing the dispensing system 100 in the middle of the room with a fan or an area with air flow; and replacing the dispensing system 100 after a certain period of time has lapsed. The directions can further include instructions for inserting refills for the volatile-bearing substrate 104 contained therein and/or on replacement of the entire dispensing system 100.

In a particular embodiment, it is contemplated that the set of user directions recites the steps of removing the dispensing system 100 from the packaging and setting the dispensing system 100 upright on a flat surface, such as a table-top, by placing one of the curved sidewalls 116b, d of the housing 106 against the surface. The directions further include the steps of placing the dispensing system 100 in a preferred room size having airflow, such as a room of about 20 cubic meters and having a room fan, and placing additional dispensing systems 100 in the room if it is large and/or to supplement protection. In the present embodiment, the directions also include the step of placing the upright dispensing system 100 away from other objects or walls so as not to block the plurality of apertures 114a, b and the portions of the peripheral vent 118 that are exposed to airflow. Even further, the directions may include the steps for mounting the dispensing system 100, such as on a wall, by adhering or docking the first or second wall 108, 110 to a surface. Further, the directions also include the step of replacing the dispensing system 100 after a certain time period has lapsed, such as replacing the system 100 every three to four months to ensure protection.

It is further contemplated that additional or alternative embodiments can be incorporated into the dispenser 102. In one embodiment, the dispenser 102 utilizes active dispersal methods for further diffusion of the volatile from at least one volatile-bearing substrate 104 received within the dispenser 102 during at least a portion of the lifetime of the substrate 104. For instance, in a non-limiting example, the dispenser 102 can include a heater(s) to aid in the dispersal of volatiles by heating a portion of the housing 106 or the internal cavity 112 therein. In another non-limiting example, the dispenser 102 may be operatively engaged with a fan within, on, or adjacent the housing 106 to aid in the dispersal of volatiles. Various means for supplying electrical power for active dispersal methods can include operatively engaging an electric plug to a wall 108, 110 of the housing 106 or any other structure thereof, engaging a battery supply or USB plug, or any other means for transporting energy to the dispenser 102. Merely by way of example, it is contemplated that the dispenser 102 utilizes passive dispersal for diffusing the volatile during a first stage, or first time period, of its lifetime when volatile concentration of the volatile-bearing substrate 104 is relatively high. In a second stage of the lifetime when a portion of the volatiles have been depleted, the dispenser 102 can be plugged into a power source, such as an electrical socket, and retained thereon for heating a portion of the housing 106 and enhancing diffusion of the remaining volatiles from the volatile-bearing substrate 104. In another aspect, diffusion of volatiles from the volatile-bearing substrate 104 can also include running a fan adjacent to one or more apertures 114a, b or a portion of the peripheral vent 118 on a sidewall 116a-d of the housing 106 or running a fan within the housing 106 in a similar manner. Furthermore, it is contemplated that stands, magnets, clips, adhesives, rubberized gripping surfaces, detents, grooves, hooks, or any other deployment mechanisms can be utilized in conjunction with the dispenser 102 for mounting purposes. Even further, it is contemplated that the dispenser 102 and/or volatile-bearing substrate 104 can comprise any variety of shapes or geometric features. For instance, it is contemplated that the number of edges of the dispenser 102 and/or volatile-bearing substrate 104 can be increased by alternative shapes, such as stars, octagons, and the like. Furthermore, the dispenser 102 can comprise regulating means, such as a plate, a rotatable cover, or a sheet(s) of non-permeable and/or permeable film, that operatively engages the housing 102 to cover at least a portion of the openings, such that a user can selectively increase or decrease the diffusion intensity. As such, the dispenser 102 can be combined with a variety of alternative embodiments to enhance its diffusion characteristics while meeting various needs of the user.

Any of the embodiments provided herein may be modified to include any of the structures or methodologies disclosed in connection with different embodiments. Further, it is contemplated that the first and second walls 108, 110 can be inseparable or separable to allow a user to replace the volatile-bearing substrate 104. It is also noted that the first and second terminology applied in describing the first and second walls 108, 110 do not imply particular deployment configurations of the dispenser 102 as a whole, and that any or all of the components disposed on either wall, such as the attachment elements described above, can be interchanged and mixed.

All documents cited in the Detailed Description of the Invention are, in relevant part, entirely incorporated herein by reference; the citation of any document is not to be construed as an admission that it is prior art with respect to the present invention.

INDUSTRIAL APPLICABILITY

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

I claim:

1. A passive volatile dispensing device, comprising:
   a housing having first and second curved walls and sidewalls therebetween; and a volatile-bearing substrate disposed within an internal cavity of the housing, wherein the first and second curved walls each include at least one aperture positioned remotely from a non-peripheral region, wherein the sidewalls each include a vent therein, wherein each vent defines a continuous vent contour that is mirrored to a contour defined by the respective sidewall in which the vent is formed, and wherein the vents in the at least two opposing sidewalls and the internal cavity combine to form an airflow path through the housing and along the volatile-bearing substrate, and wherein the airflow path promotes emanation from the volatile-bearing substrate and the non-peripheral regions direct airflow along the airflow path.

2. The passive volatile dispensing device of claim 1, wherein the volatile-bearing substrate is provided with a curve.

3. The passive volatile dispensing device of claim 2, wherein the volatile-bearing substrate comprises a pre-curved substrate.

4. The passive volatile dispensing device of claim 2, wherein the first and second curved walls impart a complementary curvature on the volatile-bearing substrate.

5. The passive volatile dispensing device of claim 1, wherein the vents combine to form a peripheral vent that traverses the sidewalls and extends circumferentially about the housing.

6. The passive volatile dispensing device of claim 5, wherein the peripheral vent comprise a peripheral gap that extends substantially continuously about the sidewalls of the housing.

7. The passive volatile dispensing device of claim 6, wherein the peripheral gap is between about 1 mm to about 10 mm wide.

8. The passive volatile dispensing device of claim 6, wherein the peripheral gap is offset from at least one edge of the volatile-bearing substrate.

9. The passive volatile dispensing device of claim 6, wherein the peripheral gap is aligned with at least one edge of the volatile-bearing substrate.

10. The passive volatile dispensing device of claim 1, wherein the volatile-bearing substrate comprises a flexible cellulosic substrate.

11. The passive volatile dispensing device of claim 1, wherein the first and second curved walls define an arcuate sidewall having a sidewall width x and a footprint width y such that y/x is from 1.5 to 2.5.

12. The passive volatile dispensing device of claim 1, wherein the volatile-bearing substrate comprises an active ingredient selected from an insecticide, an insect repellant, and an insect attractant.

13. A passive volatile dispensing device, comprising:
a housing having sidewalls and first and second curved walls, wherein the first and second curved walls define an internal cavity therebetween;
first and second substrate-retaining ribs extending through the internal cavity from the first and second curved walls, respectively, which are configured to secure a non-peripheral region of a volatile-bearing substrate; and
a gap that traverses the sidewalls and extends circumferentially about the housing, wherein a continuous gap contour defined by the gap is mirrored to a contour defined by at least one of the sidewalls, wherein the housing defines a central region that corresponds with the non-peripheral region, and wherein the central region is perforated to a lesser degree than an outer region surrounding the central region to direct airflow along the non-peripheral region to promote emanation from the volatile-bearing substrate.

14. The passive volatile dispensing device of claim 13, wherein the first and second substrate retaining ribs are configured to secure a central region of a volatile-bearing substrate.

15. The passive volatile dispensing device of claim 13, further comprising a plurality of first and second substrate-retaining ribs configured to secure a non-peripheral region of a volatile-bearing substrate.

16. The passive volatile dispensing device of claim 15, further comprising a volatile-bearing substrate retained between the plurality of first and second substrate-retaining ribs.

17. The passive volatile dispensing device of claim 13, further comprising first and second peripheral substrate retaining ribs extending through the internal cavity from the first and second curved walls, respectively.

18. A passive volatile dispensing device, comprising:
a housing having first and second curved walls and sidewalls therebetween: and
a peripheral gap that extends about the sidewalls of the housing, wherein a continuous gap contour defined by the peripheral gap is mirrored to a contour defined by the respective sidewall along which the peripheral gap extends,
wherein the first and second curved walls define an internal cavity therebetween for securing a volatile-bearing substrate therein, further wherein a central portion of at least one of the first and second curved walls has a surface area Ba that is perforated to a lesser degree than that of a peripheral region surrounding the central portion, and
wherein the central portion directs airflow within the internal cavity along a curvature of the at least one first and second curved walls toward the peripheral region to promote emanation from the volatile-bearing substrate.

19. The passive volatile dispensing device of claim 18, wherein the surface area $B_A$ of the central portion is about zero percent to about 50 percent perforated.

20. The passive volatile dispensing device of claim 19, wherein the surface area BA is less than or equal to one quarter of the surface area SA of the respective first and second curved wall.

21. The passive volatile dispensing device of claim 5, wherein one or more brackets extend from an internal surface of at least one of the first curved wall and the second curved wall adjacent corners thereof, and wherein airflow through the peripheral vent is interrupted by the brackets.

22. The passive volatile dispensing device of claim 13, wherein one or more brackets extend from an internal surface of at least one of the first curved wall and the second curved wall adjacent corners thereof, and wherein airflow through the gap is interrupted by the brackets.

23. The passive volatile dispensing device of claim 18, wherein one or more brackets extend from an internal surface of at least one of the first curved wail and the second curved wall adjacent corners thereof, and wherein airflow through the peripheral gap is interrupted by the brackets.

* * * * *

UNITED STATES PATENT AND TRADEMARK OFFICE
CERTIFICATE OF CORRECTION

PATENT NO. : 9,591,842 B2  
APPLICATION NO. : 14/015026  
DATED : March 14, 2017  
INVENTOR(S) : Paul E. Furner

Page 1 of 1

It is certified that error appears in the above-identified patent and that said Letters Patent is hereby corrected as shown below:

In the Claims

Column 15, Line 10: replace "wherein the vents in the at least two opposing sidewalls" with --wherein the vents in the sidewalls--

Signed and Sealed this  
Thirtieth Day of May, 2017

Michelle K. Lee  
*Director of the United States Patent and Trademark Office*